United States Patent [19]
Cottingham

[11] Patent Number: 5,948,673
[45] Date of Patent: *Sep. 7, 1999

[54] DEVICE AND METHOD FOR DNA AMPLIFICATION AND ASSAY

[75] Inventor: Hugh V. Cottingham, Caldwell, N.J.

[73] Assignee: Becton Dickinson and Company, Franklin Lakes, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/878,096

[22] Filed: Jun. 18, 1997

Related U.S. Application Data

[63] Continuation of application No. 08/878,096, Jun. 18, 1997, abandoned, which is a continuation of application No. 08/527,253, Sep. 12, 1995, abandoned.

[51] Int. Cl.[6] ............... C12M 1/00; C12M 1/40; G01N 33/00; C12Q 1/68
[52] U.S. Cl. ............... 435/287.2; 422/50; 435/6; 435/91.1; 435/183; 435/288.3; 435/305.1
[58] Field of Search ............... 435/6, 91.1, 183, 435/287.2, 288.3, 305.1, 305.2, 305.3, 305.4; 422/30

[56] References Cited

U.S. PATENT DOCUMENTS

| | | | |
|---|---|---|---|
| 3,694,320 | 9/1972 | Buissiere | 195/144 |
| 3,876,377 | 4/1975 | Cinqualbre | 23/253 R |
| 4,018,652 | 4/1977 | Lanham et al. | 195/103.5 |
| 4,038,151 | 7/1977 | Fadler et al. | 195/127 |
| 4,055,394 | 10/1977 | Friedman et al. | 23/253 |
| 4,076,592 | 2/1978 | Bradley | 195/103.5 |
| 4,260,392 | 4/1981 | Lee | 23/230 |
| 4,271,270 | 6/1981 | Lukacsek | 435/294 |
| 4,305,721 | 12/1981 | Bernstein | 23/230 B |
| 4,387,164 | 6/1983 | Hevey et al. | 436/45 |
| 4,596,695 | 6/1986 | Cottingham | 422/58 |
| 4,608,231 | 8/1986 | Witty et al. | 422/61 |
| 4,673,657 | 6/1987 | Christian | 436/501 |
| 4,675,299 | 6/1987 | Witty et al. | 436/165 |
| 4,708,931 | 11/1987 | Christian | 435/7 |
| 4,774,192 | 9/1988 | Terminiello et al. | 436/530 |
| 4,775,515 | 10/1988 | Cottingham | 422/73 |
| 4,891,319 | 1/1990 | Roser | 435/188 |
| 4,902,624 | 2/1990 | Columbus et al. | 435/316 |
| 5,100,626 | 3/1992 | Levin | 422/100 |
| 5,126,276 | 6/1992 | Fish et al. | 436/531 |
| 5,147,607 | 9/1992 | Mochida | 422/57 |
| 5,192,502 | 3/1993 | Attridge et al. | 422/57 |
| 5,200,321 | 4/1993 | Kidwell | 435/7.9 |
| 5,210,015 | 5/1993 | Gelfand et al. | 435/6 |
| 5,219,762 | 6/1993 | Katamine et al. | 436/518 |
| 5,229,297 | 7/1993 | Schnipelsky et al. | 435/94 |
| 5,236,827 | 8/1993 | Sussman et al. | 435/34 |
| 5,240,844 | 8/1993 | Wie et al. | 435/7.92 |
| 5,281,540 | 1/1994 | Merkh et al. | 436/530 |
| 5,314,825 | 5/1994 | Weyrauch et al. | 436/4.3 |
| 5,364,744 | 11/1994 | Buican et al. | 430/321 |
| 5,369,007 | 11/1994 | Kidwell | 435/7.9 |
| 5,372,948 | 12/1994 | Yip | 436/534 |
| 5,376,313 | 12/1994 | Kanewske, III et al. | 264/1.1 |
| 5,378,638 | 1/1995 | Deeg et al. | 436/518 |
| 5,413,924 | 5/1995 | Kosak et al. | 435/177 |
| 5,416,003 | 5/1995 | Lawrence et al. | 435/18 |
| 5,422,270 | 6/1995 | Caspi | 435/284 |
| 5,422,271 | 6/1995 | Chen et al. | 435/287 |
| 5,424,220 | 6/1995 | Goerlach-Graw et al. | 436/568 |
| 5,500,187 | 3/1996 | Deoms et al. | 422/58 |
| 5,503,985 | 4/1996 | Cathey et al. | 435/7.9 |
| 5,516,490 | 5/1996 | Sanadi | 422/101 |
| 5,545,528 | 8/1996 | Mitsuhashi et al. | 435/6 |
| 5,552,272 | 9/1996 | Bogart | 435/6 |
| 5,567,598 | 10/1996 | Stitt et al. | 435/29 |
| 5,569,607 | 10/1996 | Simon et al. | 435/46 |
| 5,576,197 | 11/1996 | Arnold | 435/91.2 |
| 5,578,270 | 11/1996 | Reichler et al. | 422/67 |
| 5,580,794 | 12/1996 | Allen | 436/169 |
| 5,585,273 | 12/1996 | Lawrence et al. | 435/288.7 |
| 5,587,128 | 12/1996 | Wilding et al. | 422/50 |
| 5,589,350 | 12/1996 | Bochner | 435/29 |
| 5,590,052 | 12/1996 | Kopf-Sill et al. | 364/498 |
| 5,604,130 | 2/1997 | Warner et al. | 435/286.7 |
| 5,639,428 | 6/1997 | Cottingham | 435/6 |

FOREIGN PATENT DOCUMENTS

| | | |
|---|---|---|
| 0215419 | 3/1987 | European Pat. Off. . |
| 0318255 | 5/1989 | European Pat. Off. . |
| 0347771 | 12/1989 | European Pat. Off. . |
| 0382433 | 8/1990 | European Pat. Off. . |
| 0512334 | 11/1992 | European Pat. Off. . |
| 0524808 | 1/1993 | European Pat. Off. . |
| 0611598 | 8/1994 | European Pat. Off. . |
| 0640828 | 3/1995 | European Pat. Off. . |
| 0723812 | 7/1996 | European Pat. Off. . |
| 9316194 | 8/1993 | WIPO . |
| 9403637 | 2/1994 | WIPO . |

OTHER PUBLICATIONS

C.M. Carlin, "Photoselection Spectrometer by a Simple Modification of a Luminescence Spectrometer", *Review of Scientific Instruments*, vol. 52, No. 1, pp. 137–138 (Jan. 1981).

Bexter Diagnostics Inc., *Scientific Products General Catalog 1991–1992*, pp. 1937–1938.

Primary Examiner—Kenneth R. Horlick
Assistant Examiner—Jeffrey Siew
Attorney, Agent, or Firm—David W. Highet, Esq.

[57] ABSTRACT

A DNA amplification and homogeneous DNA probe assay device is provided which includes a multiplicity of discrete sample cells in a flat "card" format, with each sample cell containing the reagents necessary for both DNA amplification and homogeneous DNA probe assay. The device is particularly suitable for fluorescence polarization DNA probe assays, aid is preferably provided with and integal polarizer to avoid the need for polarizing elements in the related measuring apparatus. The size and geometry of the sample cells allows for a "hot start" of the DNA amplification reaction and thereby avoids mis-priming of the amplification reaction.

11 Claims, 13 Drawing Sheets

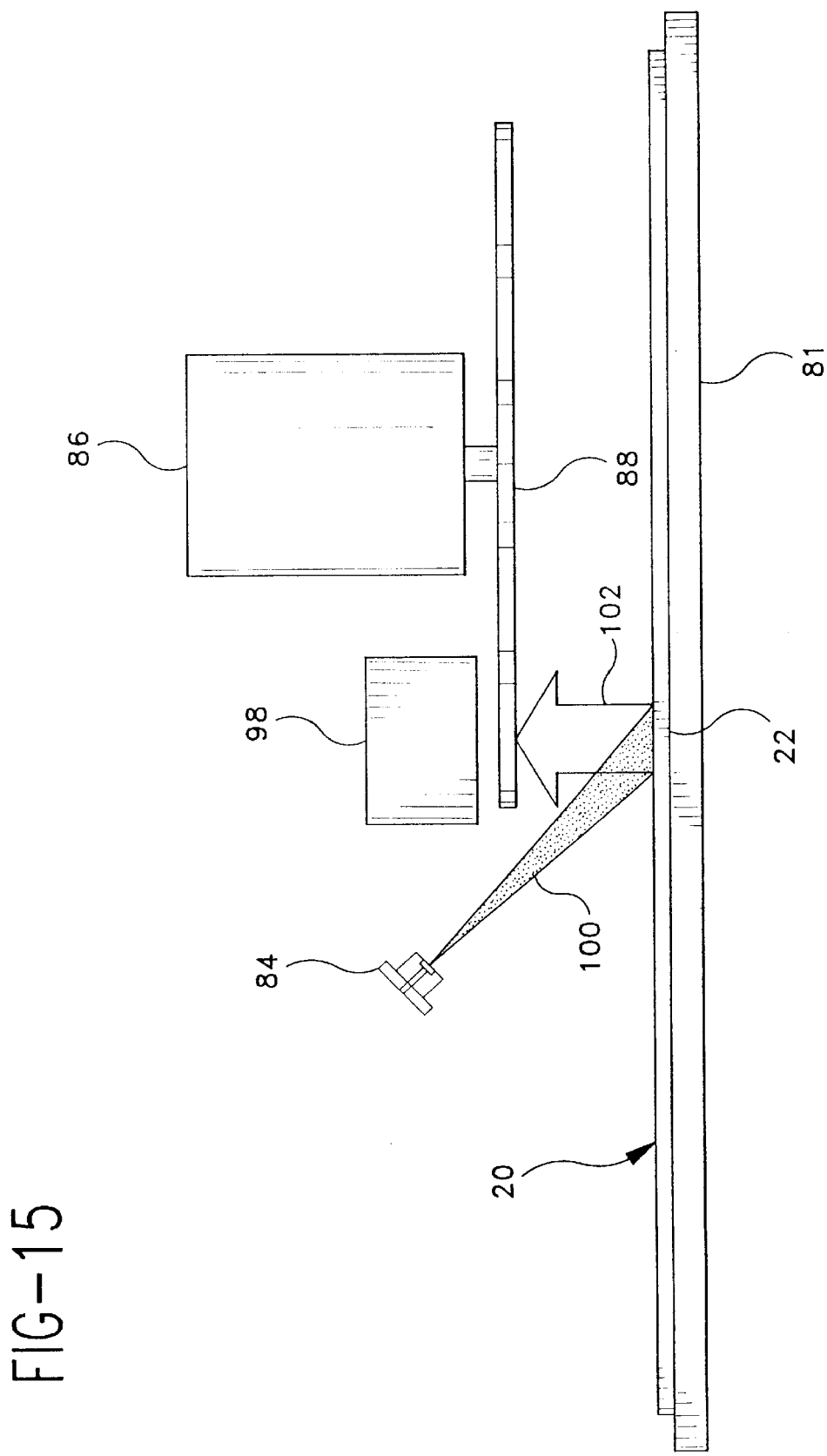

DEVICE AND METHOD FOR DNA AMPLIFICATION AND ASSAY

This is a continuation of U.S. patent application Ser. No. 08/878,096, filed Jun. 18, 1997, now abandoned, which is a continuation of U.S. patent application Ser. No. 08/527,253, filed Sep. 12, 1995, now abandoned.

FIELD OF THE INVENTION

The present invention relates generally to devices and methods for carrying out biological processes on liquid biological samples, and is particularly concerned with a unitary DNA amplification and homogenous DNA probe assay device which is suited for fluorescence polarization assays and is capable of accommodating a plurality of liquid biological samples in discrete, sealed sample cells.

BACKGROUND OF THE INVENTION

The processes of nucleic acid (DNA) amplification and subsequent nucleic acid probe assay are well known and have been implemented in a variety of formats. While these formats are highly effective, they are somewhat difficult to perform in the clinical laboratory. Generally, DNA amplification and assay reactions are performed sequentially on the sample to be assayed; that is, the DNA amplification reaction is first carried out to completion, and the DNA probe assay is then performed on the fully amplified sample. This is referred to as an end point assay.

One problem with end point assays is that the amplified DNA (amplicons) from the DNA amplification reaction must be physically transferred to the subsequent DNA probe assay. Because of the transfer, the potential exists for contaminating the laboratory environment with the DNA amplicons. In addition, the general risk of misidentifying a given sample or coiinfusing it with other samples increases each time that a physical transfer of the sample takes place.

There have been previous proposals for self-contained test units that are capable of carrying out an integrated nucleic acid ampliffcation and nucleic acid assay on a liquid biological sample while the sample remains confined within the test unit. For example, U.S. Pat. No. 5,229,297, to Paul N. Schnipelsky et al, describes a cuvette for DNA amplification and detection which comprises a plurality of flexible compartments for containing a sample, ampliiying reagents and detection reagents, together with passageways connecting the sample and reagent compartments with a detection site and waste compartment. A roller is used to squeeze or compress the sample and reagent compartments in a desired sequence, thereby forcing the sample and detection reagents through the passageways to the detection site and waste compartment. Teraporary seals are used to isolate the sample and reagent compartments from the passageways until sufficient pressure is generated by the roller. Although this arrangement is advantageous in that the sample remains within the cuvette during amplification and detection, the need for a roller to break the temporary seals and cause the various fluids to flow between compartments introduces undesirable complexity and makes it difficult to automate the amplification and assay procedure.

In U.S. patent application Ser. No. 08/277,553, U.S. Pat. No. 5,639,428 fled by Hugh V. Cottingham on Jul. 19, 1994, an improved test unit for carrying out integrated nucleic acid amplifications and nucleic acid assays is disclosed. In the improved test unit, the flow of sample and reagent liquids is controlled by centrifugal force applied by a relatively simple rotating apparatus, thereby avoiding the need for rollers and other complex mechanisms. While this represents a substantial improvement over the arrangement disclosed in U.S. Pat. No. 5,229,297, the need to provide for controlled fluid movement within the test unit still exists and renders the test unit somewhat more complex than might be desired.

In addition to the end point assays discussed previously, homogenous methods of nucleic acid assay also exist. Homogeneous methods do not require the physical transfer of the amplified material to a separate assay site, but rather function simultaneously with the amplification reaction. Examples of known homogenous assay methods include fluorescence polarization, fluorescence energy transfer and light absorbance. While fluorescence polarization, in particular, functions very well in a research laboratory, it has a significant drawback in that it requires glass sample tubes or cells. This is a result of the fact that most plastic processing methods, such as injection molding or thermoforming, create stresses in the material of the finished part. These stresses have random polarization effects, and interfere with the transmission of polarized light that is required for a fluorescence polaization assay.

As is well known, DNA amplification reactions must occur within a certain temperature range in order to produce the desired number of amplicons. If the sample and the DNA amplification reagents are allowed to react before the sample reaches the required temperature, a phenomenon known as "mis-priming" can occur. This can affect the validity of the assay results, both in the case of an end point assay and a homogeneous assay.

In view of the foregoing, a need exists for a device or a test unit which is capable of carrying out an integrated DNA amplification and DNA probe assay with minimal complexity, and preferably without requiring fluid movements to occur within the test unit itself. There is also a need for a test unit which can be used to carry out a homogenous DNA probe assay using fluorescence polarization methods, but which does not require the use of glass to properly transmit polarized light. Finally, there exists a need for a test unit which can be used to carry out an integrated DNA amplification and DNA probe assay in a simple and effective manner, while preventing inadvertent mis-priming of the amplification reaction. The present invention is directed to fulfilling these objectives.

It is an object of the present invention to provide a DNVA amplification and homogenous DNA probe assay device in a "card" format that can be conveniently handled by clinical laboratory personnel, and accommodated in a suitable test apparatus.

It is another object of the invention to provide a unitary DNA amplification and DNA probe assay device which includes a multiplicity of sample cells, with each sample cell comprising the element and reagents needed for a DNA amplification reaction and a homogeneous DNA probe assay.

It is a further object of the invention to provide a unitary DNA amplification and DNA probe assay device in which all reagents needed for both DNA amplification and DNA probe assay are contained, in dried form, within the device, so that the addition of a liquid biological sample is all that is needed to carry out the amplification and assay procedure.

It is a further object of the invention to provide a test unit and method that performs a "hot start" of the DNA amplification reaction, thereby avoiding an invalid assay result due to mis-priming of the amplification reaction.

It is a further object of the invention to provide a test unit which has the optical properties necessary for a fluorescence polarization assay, but which can be made of inexpensive plastic materials rather than glass.

It is a further object of the invention to provide a test unit and method that yields instantaneous DNA probe assay data by means of a kinetic or dynamic measurement of DNA amplicons, rather than a conventional end point measurement.

It is a further object of the invention to provide a fluorescence polarzation DNA probe assay device which includes an integral polarizer, allowing for the use of a confocal polarization method.

It is a further object of the invention to provide an integral DNA amplification and homogenous DNA probe assay device that can be permanently sealed after the introduction of a liquid biological sample, thereby preventing amplicon contamination of the laboratory environment.

It is a still further object of the invention to provide an integrated DNA amplification and DNA probe assay device which can accommodate a plurality of liquid biological samples in discrete sample cells, and which can provide DNA probe assay data in a matter of minutes.

SUMMARY OF THE INVENTION

In accordance with a preferred embodiment of the present invention, the disadvantages and limitations of the prior art are substantially avoided by providing a DNA amplification and homogeneous DNA probe assay device which includes a multiplicity of discrete sample cells in a flat "card" format, with each sample cell containing the reagents necessary for both DNA amplification and homogeneous DNA probe assay. The device is particularly suitable for fluorescence polarization DNA probe assays, and is preferably provided with an integral polarizer to avoid the need for polarizing elements in the related measuring apparatus. The size and geometry of the sample cells allows for a "hot start" of the DNA amplification reaction and thereby avoids inadvertent mis-priming of the amplification reaction.

In one aspect, the present invention is directed to an apparatus for carrying out a nucleic acid amplification and a homogeneous nucleic acid assay on a liquid biological sample. The apparatus includes a sample cell for receiving the liquid biological sample. The sample cell includes a sample chamber and a sample port for admitting the liquid biological sample into the sample chamber. A dried nucleic acid amplification reagent and a dried homogeneous nucleic acid assay reagent are adhered to the interior of the sample chamber for reacting with the liquid biological sample. A sealing member may be attached to the sample cell for sealing the sample port after the liquid biological sample has been admitted to the sample chamber. The homogeneous nucleic acid assay reagent may comprise a fluorescence polarization assay reagent, and in that event a portion of the sample cell may be made transparent to permit external detection of the fluorescence polarization reaction in the liquid biological sample. The sealing member may be attachable over the transparent portion of the sample chamber and may be made of a transparent, light-polarizing material to avoid the need for polarizing elements in the related measuring apparatus.

In another aspect, the present invention is directed to an apparatus for carrying out a biological process on a liquid biological sample. The apparatus comprises a substantially flat, card-like member having at least one sample cell therein for receiving the liquid biological sample. The sample cell includes a sample chamber, a sample port for admitting the liquid biological sample into the sample chamber, an air vent for allowing air to be displaced from the sample chamber during admission of the liquid biological sample into the sample chamber, and a dried reagent adhered to an internal surface of the sample chamber for reacting with the liquid biological sample. A sealing member, preferably in the form of a layer of flexible material carrying a pressure-sensitive adhesive, is attachable to the card-like member for sealing the sample port and the air vent after a liquid biological sample has been admitted to the sample chamber.

In another aspect, the present invention is directed to an apparatus for carrying out a nucleic acid fluorescence polarization assay on a liquid biological sample. The apparatus includes a sample cell for receiving a liquid biological sample. The sample cell has a sample chamber and a sample port for admitting the liquid biological sample into the sample chamber. The apparatus also comprises a dried nucleic acid fluorescence polarization reagent that is adhered to an internal surface of the sample chamber for reacting with the liquid biological sample. At least a portion of the sample cell is made of a light-transmissive, light-polarizing material to facilitate external detection of the fluorescence polarization reaction in the liquid biological sample without the need for separate polarization elements in the related measuring apparatus.

In a further aspect, the present invention is directed to a method for carrying out an integrated nucleic acid amplification and homogeneous nucleic acid fluorescence polarization assay on a liquid biological sample. The method comprises the steps of introducing a liquid biological sample into a sample well having a light-transmissive portion; bringing the liquid biological sample into contact with a dried nucleic acid amplification reagent and a dried homogeneous nucleic acid fluorescence polarization assay reagent within the sample cell; sealing the sample cell; incubating the sample cell to allow the liquid biological sample to react with the nucleic acid amplification reagent and with the homogeneous nucleic acid fluorescence polarization assay reagent; and detecting fluorescence polarization in the liquid biological sample through the light-transmissive portion of the sample cell. The detection step may comprise directing polarized light through the light-transmissive portion of the sample cell or, if the light-transmissive portion of the sample cell is made of a light-polarzing material, directing unpolarized light through the light-transmissive portion of the sample cell.

In a still further aspect, the present invention is directed to a method for carrying out a nucleic acid amplification reaction on a liquid biological sample. The method comprises the steps of preheating a sample cell containing an dried nucleic acid amplification reagent to a temperature suitable for nucleic acid amplification; introducing a liquid biological sample into the preheated sample cell to bring the liquid biological sample into contact with the dried nucleic acid amplification reagent; equilibrating the temperature of the liquid biological sample to the temperature of the preheated sample cell; and, after the equilibration is substantially complete, commencing the nucleic acid amplification reaction in the sample cell. Preferably, the step of equilibrating the temperature of the liquid biological sample to the temperature of the preheated sample cell comprises forming a thin layer of the liquid biological sample in the sample cell to enhance heat transfer between the sample cell and the liquid biological sample.

BRIEF DESCRIPTION OF THE DRAWINGS

The various objects, advantages and novel features of the invention will be more readily appreciated from the following detailed description when read in conjunction with the appended drawing figures, in which:

FIG. 5 is a plan view of the top layer of the DNA amplification and DNA probe assay card of FIGS. 1–4, illustrating the manner in which sample ports and air vents are provided for the discrete sample cells;

FIGS. 13–15 illustrate an exemplary measuring apparatus which can be used to measure fluorescence intensity in the sample cells of the DNA amplification and DNA probe assay card of FIGS. 1–4.

Throughout the drawings, like reference numerals will be understood to refer to like parts and components.

DETAILED DESCRIPTION OF THE PREFERRED EMBODIMENTS

Figure 1:
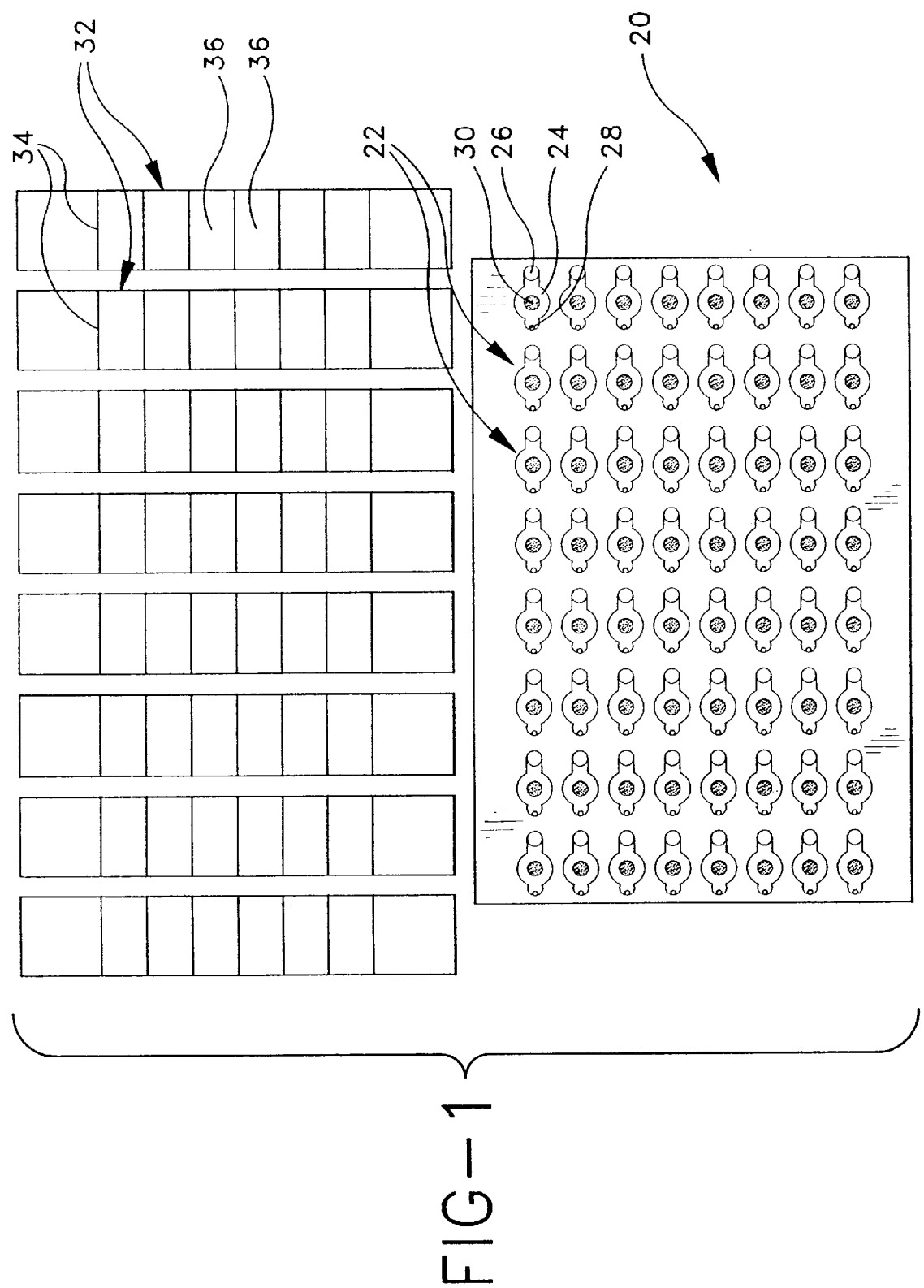
FIG. 1 is a top view of a DNA amplification and homogeneous DNA probe assay card constructed in accordance with a preferred embodiment of the present invention, illustrating separate sealing strips which are used to seal the individual sample cells of the card after liquid biological samples have been introduced into the sample cells.

A DNA amplification and homogeneous DNA probe assay device 20 (hereinafter referred to as a "DNA card") constructed in accordance with a preferred embodiment of the present invention is illustrated in FIG. 1. Although the specific dimensions and geometry of the DNA card may be varied in accordance with the requirements of particular applications, the card 20 of the preferred embodiment is rectangular with a length of approximately 5.025 inches and a width of approximately 3.362 inches. The card contains a rectangular array of discrete sample cells 22, spaced evenly across the length send width of the card. Each sample cell 22 includes a closed sample chamber 24 (the top wall of which is transparent) for receiving a liquid biological sample, an open sample port 26 which communicates with the sample chamber 24, and an air vent 28 which also communicates with the sample chamber 24. Dried DNA amplification and assay reagents are adhered to the upper interior wall of each sample cell 22 in the form of a single, discrete spot 30. The sample ports 26 provides the means by which liquid biological samples (not shown in FIG. 1) can be introduced into each of the sample chambers 24 (preferably by pipetting), and the air vents 28 allows air to be displaced from the sample chambers 24 as the liquid biological samples are being introduced. As will be described hereinafter, the liquid biological sample that is introduced into the sample chamber 24 of each sample cell 22 makes contact with, and dissolves, the dried reagent spot 30 in the sample cell, thereby initiating the desired DNA amplification and assay reactions. Measurement of the assay results takes place while the liquid biological samples remain sealed within the sample cells 22, also in a manner to be described hereinafter. In the illustrated embodiment, the DNA card 20 contains sixty-four (64) identical sample cells 22, arranged in a rectangular array of eight rows by eight columns, on vertical centers of approximately 0.354 inches and hoizontal centers of approximately 0.628 inches.

With continued reference to FIG. 1, sealing strips 32 (one for each column of sample cells 22 in the card 20) are provided for sealing the sample ports 26 and air vents 28 of the sample chambers 24 after liquid biological samples have been introduced into the sample cells 22. Preferably, the strips 32 are segmented along score lines 34 to define segments which can be used individually, if desired, to seal some of the sample cells 22 and not others. In the illustrated embodiment, the sealing strips 32 are approximately 0.628 inches in width and approximately 3.362 inches in length. Each sealing strip 212 seals a column of eight sample cells 22, with eight strips 32 being used to seal all sixty-four sample cells 22. The individual segments or seals 36 of each seaihgk strip 32 are on the same vertical centers (i.e., approximately 0.354 inches apart) as the sample cells 22 themselves. The sealing strips 32 are preferably about 0.015 inches thick and are provided with a layer of pressure sensitive adhesive or their lower surfaces (not visible in FIG. 1). In practice, the sealing strips 32 are applied in a manner similar to adhesive tape, and serve to permanently seal the sample cells 22 by covering the sample ports 26 and air vents 28. The sealing strips 32 are generally used whole for convenience, and are only subdivided as necessary along the score lines 34.

The sealing of the sample cells 22 by means of the sealing strips 32 provides several advantages. First, the sealing strips 32 prevent evaporation of the liquid biological samples from the sample cells 22 during the DNA amplification and homogeneous DNA probe assay. Given that, the volume of the liquid biological sample will typically be very small (about 20 µL) and that the amplification and assay reactions will usually take place at an elevated temperature (up to about 75° C.), such evaporation may otherwise result in significant loss of the liquid biological sample. The second advantage of the sealing strips 32 is that they prevent the release of DNA amplicons from the sample cells 22, thereby preventing contamination of the laboratory environment. Finally, in accordance with a particularly preferred embodiment of the present invention, the sealing strips 32 may be made of a transparent, light-polarizing material so as to serve as polarization elements during the detection or measurement step. This avoids the need to provide separate polarization elements in the related measuring apparatus.

In the description which follows, it will be assumed that all of the sample cells 22 and seals 36 are identical, and that the description of any one sample cell 22 or seal 36 will apply to all. Although this is true in the preferred embodiment, the invention should not be regarded as being limited to this arrangement. It is within the scope of the invention to provide sample cells 22 and/or seals 36 that are different from one to the next, including (but not limited to) different reagents, different dimensions, different volumes and different optical properties. The reagents may differ for either the DNA amplification or the DNA probe assay, or both, with exemplary homogeneous DNA probe assay methods including fluorescence polarization reactions, fluorescence energy transfer reactions and light absorbance reactions. Any or all of the foregoing differences may exist within a single card 20 and/or from one card 20 to the next. Thus, for example, different types of DNA cards 20 could be provided for carrying out different types of assays, with such cards retaining only a generic or functioned simllarity (e.g., to the extent necessary to fit into the same type of measuring instrument).

Figure 2:
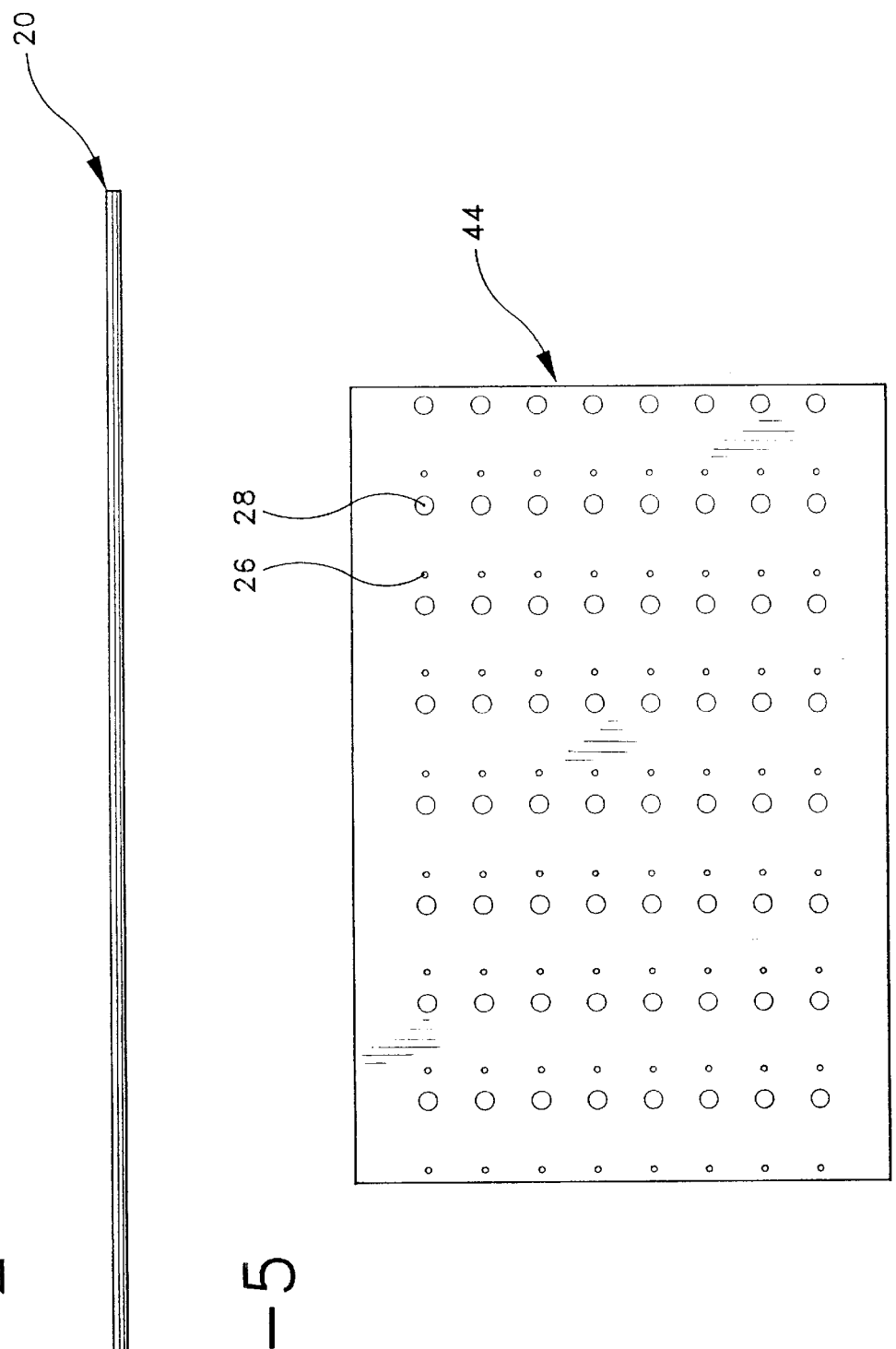
FIG. 2 is a side view of the DNA amplification and DNA probe assay card of FIG. 1, illustrating its relatively small thickness.

FIG. 2 is a side or edge-on view of the DNA card 20, which in the preferred embodiment has a generally flat or planar configuration. As will be apparent from FIG. 2, the DNA card 20 can be made extremely thin if desired. In the preferred embodiment, the thickness of the DNA card 20 is approximately 0.047 inch.

Figure 3:
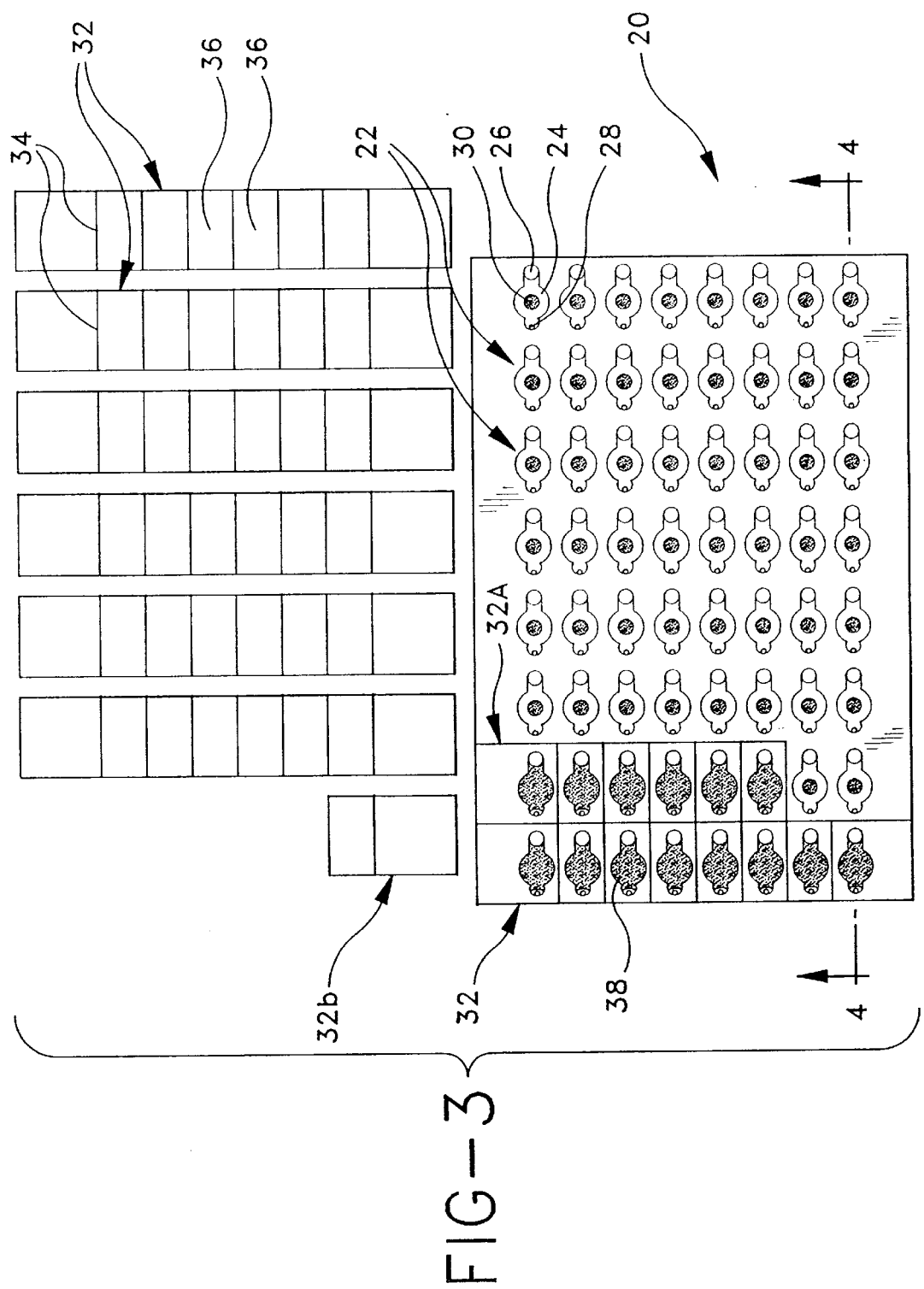
FIG. 3 is a top view of the DNA amplification and DNA probe assay card and sealing strips of FIG. 1, with some of the sample cells shown filled with liquid biological samples and sealed using the sealing strips.

FIG. 3. illustrates the DNA card 20 as it might appear during actual use, with fourteen of the sample cells 22 filled with liquid biological samples 38. In these filled sample cells 22, the liquid biological samples 38 have dissolved the dried reagent spots 30 of FIG. 1. The filled sample cells 22 are covered by the respective segments or seals 36 of the sealing strips 32. One complete sealing strip 32 has been applied to the left-hand column of sample cells 22, and a second sealing strip 32 has been subdivided along one of the score lines 34 into a first portion 32A which has been applied to the upper six sample cells 22 of the second column, and a second portion 33B which has been retained for future use. The unused portion 32B can be used to seal the two lowermost sample cells 22 of the second column during a subsequent use of the DNA card 20).

Typically, the various liquid biological samples 38 shown in FIG. 3 will consist of blood samples or other body fluid samples from different patients, all of which are being tested for the same pathogen by identical amplification and assay reagents 30. However, it will be understood that embodiments are possible in which more than one of the liquid biological samples 38 are drawn from the same patient, and in which the reagents 30 differ from one sample cell 22 to the next.

Figure 4:
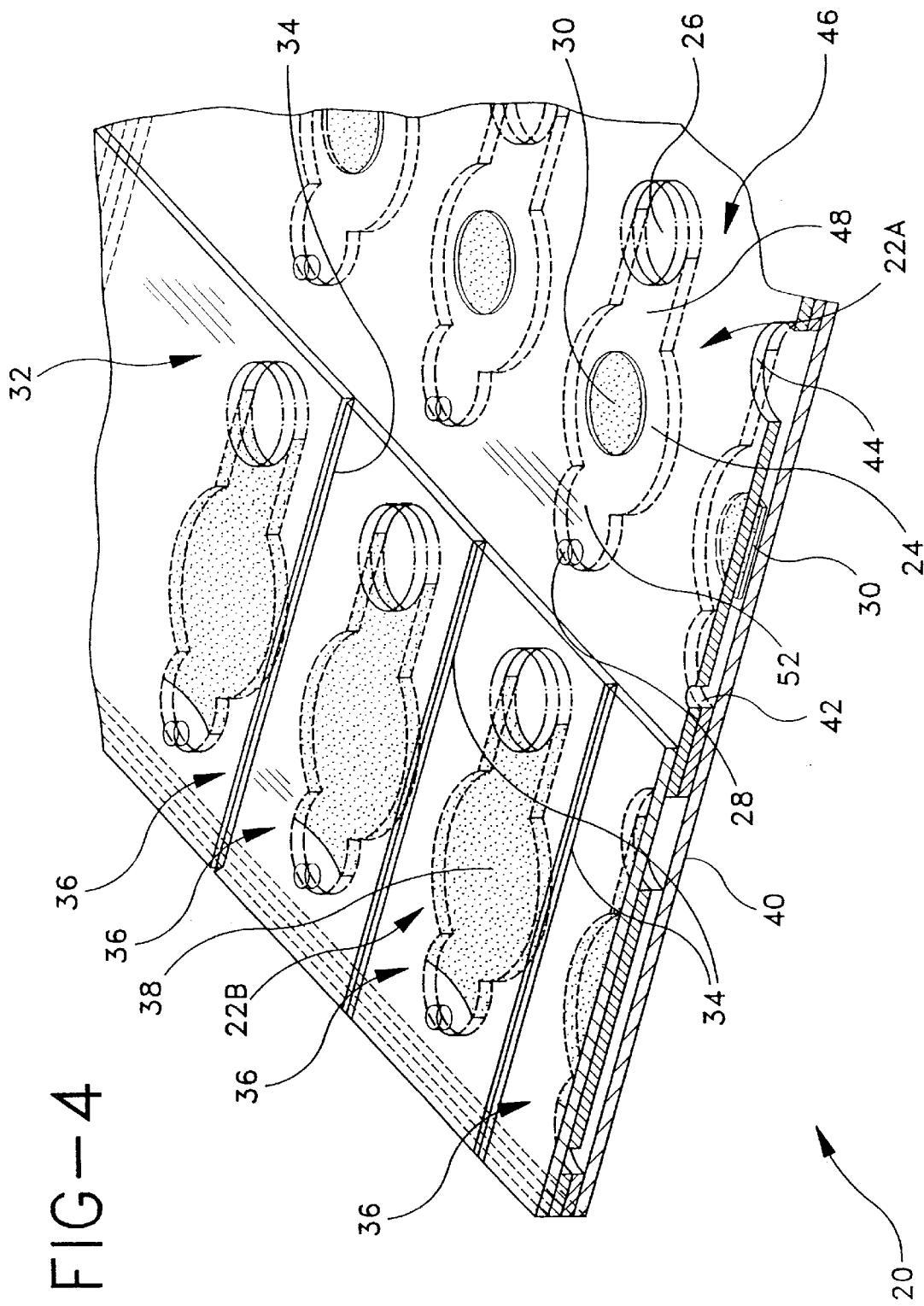
FIG. 4 is an enlarged cross-sectional view of a portion of the DNA amplification and DNA probe assay card of FIGS. 1–3, with some of the discrete sample cells shown filled and others left empty to illustrate the locations of the dried amplification and assay reagents.

FIG. 4 is a partial cross-sectional view of the DNA card 20, taken along the line 4—4 in FIG. 3. In this view, the laminated construction of the DNA card 20 in the preferred embodiment can be readily appreciated. The DNA card 20 is made up of a bottom layer 40, a middle layer 42 and a top layer 44. The seals 36 of the sealing strip 32 are adhered to the upper surface 46 of the top layer 44. Each of the layers 40, 42 and 44 is preferably made of a plastic film having a thickness of approximately 0.015 inches, and the seals 36 are of a similar material and thickness. The layers 40, 42 and 44 (together with the seals 36) are held together by a pressure-sensitive adhesive (not shown) that is typically about 0.001 inch thick. Referring for convenience to the empty sample cell 22A in FIG. 4, the sample port 26 is preferably about 0.125 inch in diameter and communicates with a narrow section 48 of the sample chamber 24 that is preferably about 0.125 inch wide. The narrow section 48, in turn, communicates with a larger, substantially circular portion of the sample chamber 24 which is approximately 0.250 inch in diameter. The dried reagent spot 30 is adhered to the upper wall of the circular portion of the sample cell 24 (corresponding to the lower surface of the top layer 44 of the DNA card) and is situated approximately at the center of this circular portion. The circular portion of the sample chamber 24 communicates with another narrow section 52 of the sample chamber which is approximately 0.125 inch in diameter. The section 52, in turn, communicates with the air vent 28 located at the opposite end of the sample cell 22A from the sample port 26. The air vent 28 is preferably about 0.040 inch in diameter. The height of the interior of the sample chamber 24 is defined by the thickness of the middle layer 42 of the DNA card 20, and by the thickness of the adhesive on either side of this layer. This results in an overall height of about 0.017 inch for the interior of the sample chamber 24.

With continued reference to FIG. 4, the sample cell. 22B is shown as it would appear during use. Thus, the sample cell 22B is filled with a liquid biological sample 38 and sealed with a seal 36 which covers the sample port 26 and air vent 28. The dried reagent spot 30 of FIG. 1 has been dissolved by the liquid biological sample 38.

In order to use the DNA card 20, a suitable measuring instrument is required. Depending upon whether the DNA card 20 contains assay reagents for fluorescence polarization reactions, fluorescence energy transfer reactions or light absorbance reactions, and whether (in the case of a fluorescence polariration assay) the DNA card 20 has integral polarizing elements, the instrument may be either a conventional instrument, such as a microplate fluorometer or a microplate reader, or a specialized instrument of the type to be described shortly in connection FIGS. 13–15. In either case, suitable temperature controls must be provided, together with means for optically addressing the individual sample cells 22.

In order to perform an integrated DNA amplification and homogeneous DNA fluorescence polarization assay, the DNA card 20 is placed on the heated carrier of the instrument. The carrier is a heated tray which can be extended outside the instrument to receive the card, and which then withdraws into the instrument in order to perform the desired readings of fluoreiscence polarization, fluorescence intensity or light absorbance. Typically, the instrument is provided with means for moving the card in both the x and y directions so that each sample cell 22 can be read individually. During the entire operation, the heated carrier maintains the DNA card 20 at an optimum temperature, typically between 25° C. and 75° C.

Initially, an empty DNA card 20 is placed on the extended, heated carrier of the instrument and is allowed to equilibrate to the carrier temperature. This equilibration may take approximately one minute. Once the DNA card 20 is equilibrated to the carrier temperature, liquid biological samples 38 are pipetted into the sample ports 26 of one or more of the sample cells 22. The liquid biological samples 38 instantly fill the sample chambers 24 due to a combination of hydrostatic and capillary force. In the preferred embodiment, the pipetted volume of each liquid biological sample is approximately 20 $\mu$L.

As soon as liquid biological samples 38 have been pipetted into all of the sample chambers 24, the sample cells 22 may be sealed using the seals 36, and the measuring instrument may be started. The carrier is then drawn into the instrument for fluorescence polarization, fluorescence intensity or light absorbance reading. Due to the extreme thinness of the sample chambers 24, and the large surface area of the sample chambers 24 with which the liquid biological samples 38 come into contact, the liquid biological samples 38 heat up within seconds of being pipetted into the sample cells 22 to the optimum temperature desired for DNA amplification. Thus, by the time the dried reagent spots 30 dissolve and diffuse throughout the liquid biological samples 38 to begin "priming" of the DNA amplification, the reagents are already up to the optimum temperature. It is in this way that the DNA card 20 effects a "hot start" of the DNA amplification reaction.

Figure 6:
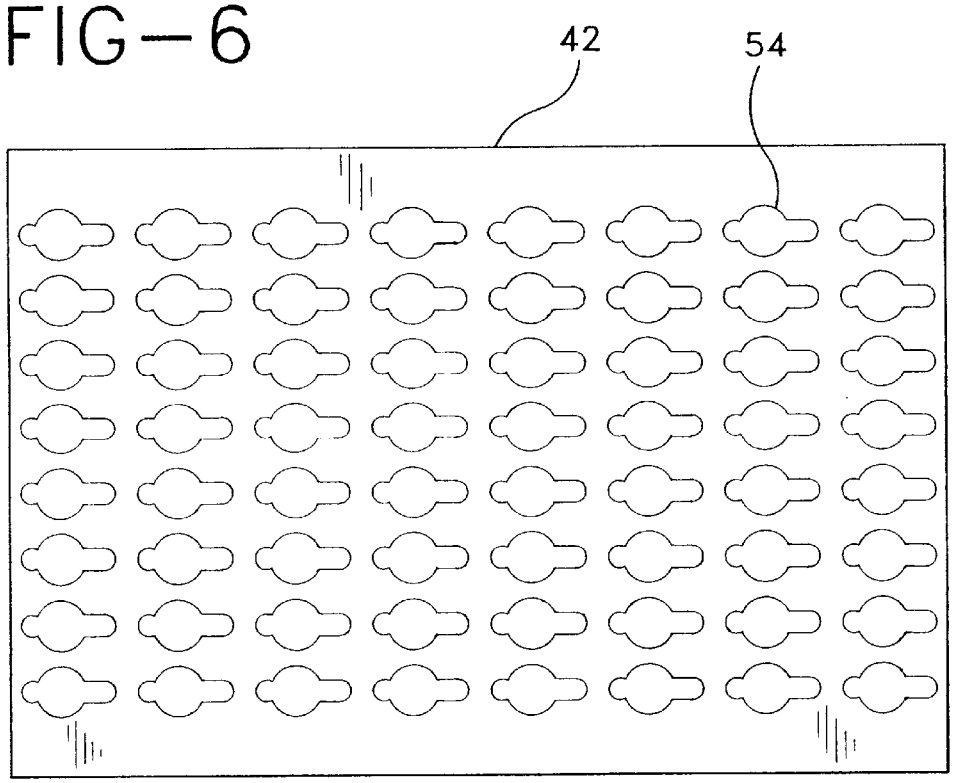
FIG. 6 is a plan view of the middle layer of the DNA amplification and DNA probe assay card of FIGS. 1–4, illustrating the keyhole-shaped apertures which define the side walls of the discrete sample cells.
Figure 7:
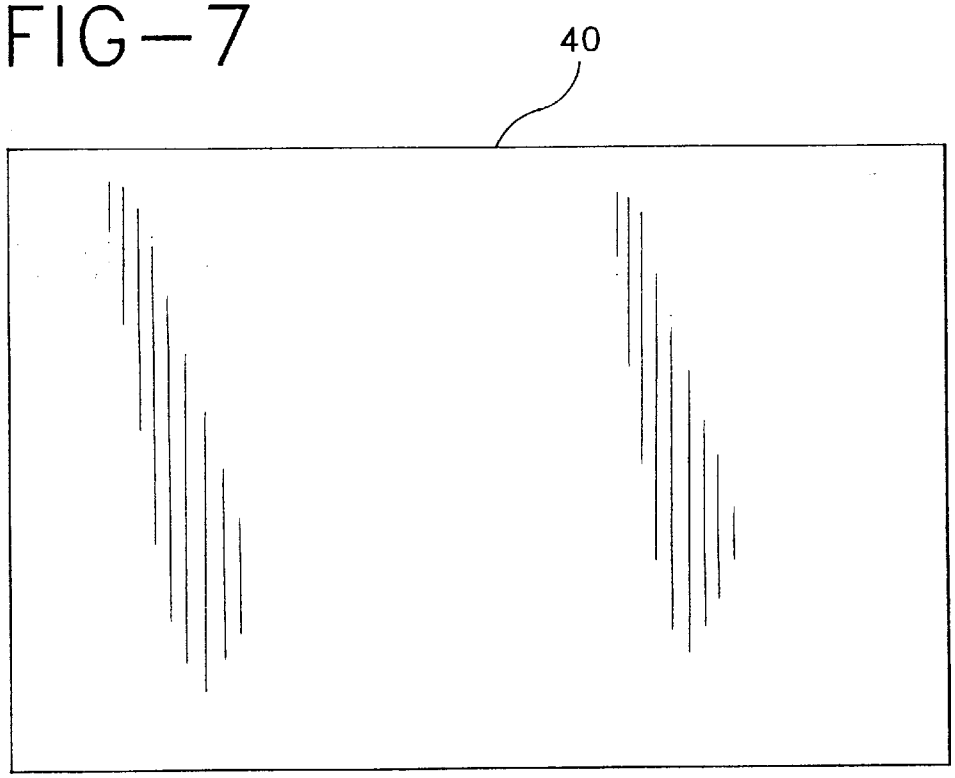
FIG. 7 is a plan view of the bottom layer of the DNA amplification and DNA probe assay card of FIGS. 1–4.

FIGS. 5–7 depict the individual layers of plastic film that the DNA card 20 is composed of. In the preferred embodiment, each layer is approximately 0.015 inch thick. The top layer 44, shown in FIG. 5, contains the holes that form the sample ports 26 and air vents 28. The lower surface of the top layer 44 forms the upper walls of the sample chambers 24. The middle layer 42, shown in FIG. 6, contains keyhole-shaped apertures 54 that form the side walls of the sample chambers 24. The middle layer 42 is coated on both sides with a pressure-sensitive adhesive (not shown). The bottom layer 40, shown in FIG. 7, is a solid rectangular sheet that forms the bottom of the DNA card 20. The upper surface of the bottom layer 40 forms the lower wall of each of the sample chambers 24.

Figure 8:
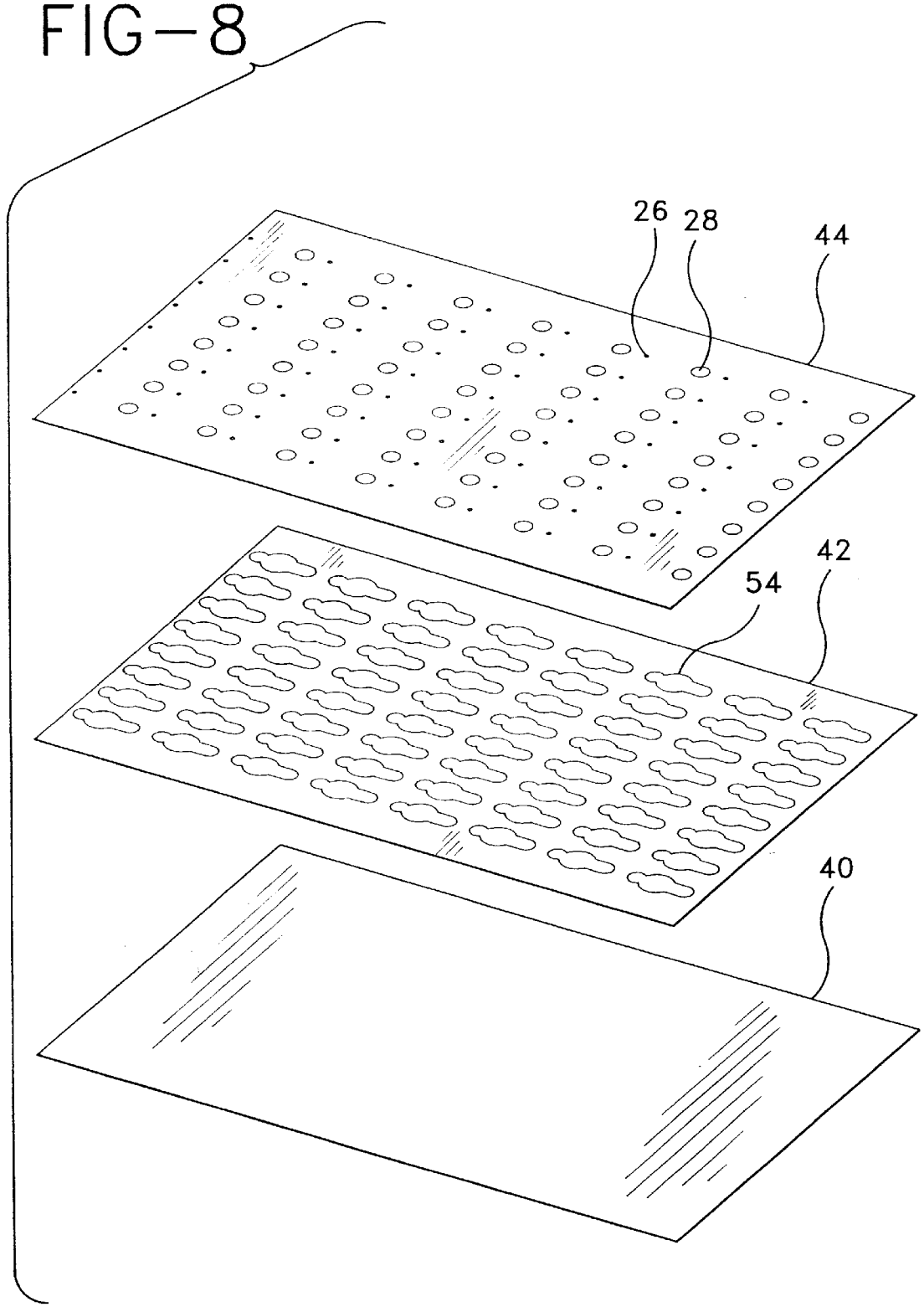
FIG. 8 is an exploded perspective view illustrating the relationship of the top, middle and bottom layers of the DNA amplification and DNA probe assay card of FIGS. 1–4.

The exploded view of FIG. 8 depicts the relative alignment of the top layer 44, middle layer 42 and bottom layer 40 during assembly of the DNA card 20. In practice, the top layer 44 and middle layer 42 are laminated together with a suitable adhesive, and the partial assembly is then inverted so that the amplification and assay reagents can be pipetted and dried onto the underside of the top layer 44 to create the dried reagent spots 30. With reference to FIG. 4, the sectioned edge of the DNA card 20 can be seen to include a dried reagent spot 30 that is adhered to the underside of the top layer 44 of the card 20. After the dried reagent spot 30 is formed, the bottom layer 40 is laminated to the middle layer 42, as shown in FIG. 8, to complete the assembly 20.

The dried reagent spot 30 contains both DNA amplification and homogeneous DNA assay reagents, the latter preferably consisting of fluorescence polarization assay reagents. Examples of suitable DNA amplification and DNA fluorescence polarization assay reagents are disclosed in copending U.S. patent application Ser. No. 08/311,474, filed by G. Terrance Walker et al on Sep. 23, 1995 and entitled "Fluorescence Polarization Detection of Nucleic Acid Amplification", said application being expressly incorporated lierein by reference. The chemical reagents in the dried spot 30 are carried in a readily soluble matrix, such a trehalose or another carbohydrate. These reagents will spontaneously re-suspend when exposed to an aqueous sample introduced into the sample chamber 24. It will be understood that more than one dried reagent spot 30 may be provided in each sample cell 22 if desired, as for example by providing the amplification reagents in one spot and the assay reagents in a different spot. In the case of a DNA amplification and homogeneous DNA assay, however, the reagent spots (if separated) should be positioned in such a way that they are dissolved by the liquid biological sample 38 at essentially the same time.

If the homogeneous DNA assay that is to be used in the DNA card 20 is a fluorescence polarization assay, the top layer 44 of the card 20 must be made of a material that does not interfere with the transmission of polarized light. Two examples of materials that satisfy this requirement are cellulose acetate butyrate (CAB) and triacetate cellulose (TAC).

Figure 9B:
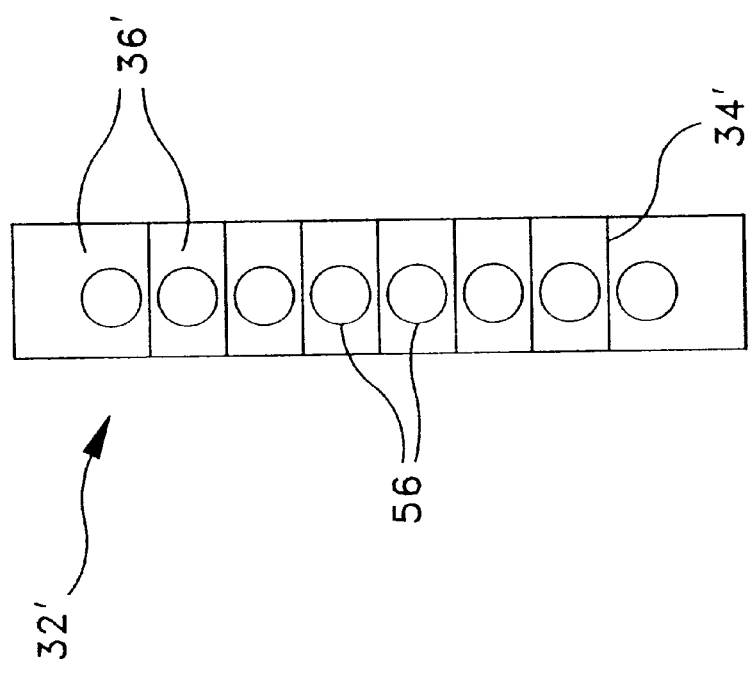
FIGS. 9A and 9B are top view of two different embodiments of the sealing strips that are used to seal the sample ports and air vents of the DNA amplification and DNA probe assay card of FIGS. 1–4.
Figure 9A:
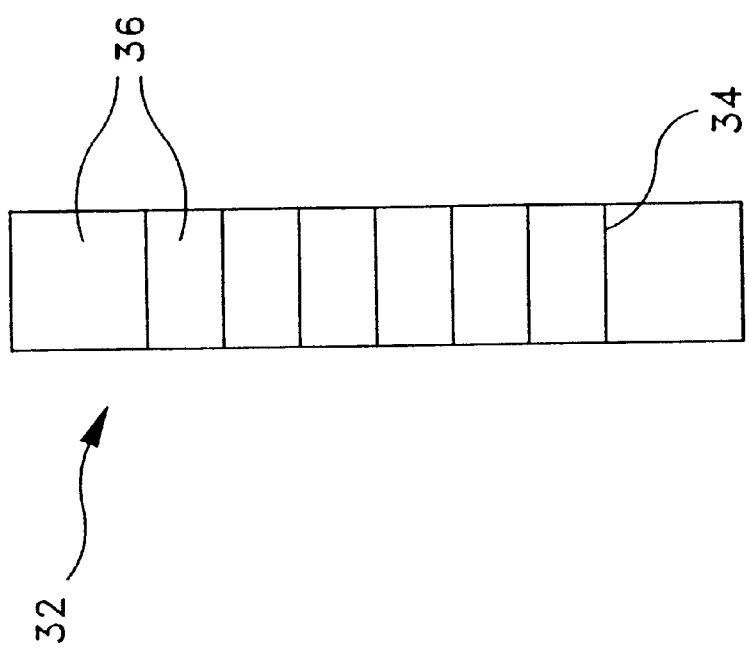

Two alternative embodiments of the sealing strip 32 are illustrated in FIGS. 9A and 9B, respectively. In FIG. 9A, the sealing strip 32 is made either of a transparent CAB having a thickness of about 0.015 inch, with an optically clear pressure-sensitive adhesive (such as Adhesives Research type 8154) applied to its back surface, or of a transparent light-polarizing film with am optically clear pressure-sensitive adhesive applied to its back surface. A suitable adhesive-backed polarizing film is available from Nitto Denko as product number 1220 DU. As previously mentioned, score lines 34 are provided to allow the sealing strip 32 to be separated into individual seals or segments 36 and shown in FIG. 3. In FIG. 9B, a modified sealing strip 32' is shown in which each of the segments or seals 36 has a central hole or aperture 56. The holes 56 allow with the central circular areas of the sample chambers 24 when the seals 36 are applied to the sample cells 22 as illustrated in FIGS. 3 and 4. The sealing strip 32' of FIG. 9B is similar to the sealing strip 32 of FIG. 9A in that it carries a layer of pressure-sensitive adhesive on its back surface, but the sealing strip 32' of FIG. 9B may be made of an opaque material (such as black PVC or CAB) since the holes 56 allow for light transmission to and from the sample chambers 24 through the top layer 44 of the DNA card 20. The sealing strip 32' of FIG. 9B is advantageous in that the light emitted by the liquid biological samples 38 during the fluorescence polarization assay is required to travel only through the top layer 44 of the DNA card 20, rather than through the top layer 44 and the sealing strip 32 as in the embodiment of FIG. 9A.

In fluorescence polarization assays, a polarized excitation beam of a given wavelength of light is used to excite the fluorescent DNA probes. The intensity, at a given wavelength, of fluorescent emission from these excited probes is measured in the plane polarized parallel to the excitation polarization, and also in the plane polarized perpendicular to the excitation polarization. When a fluorescent DNA probe hybridizes to a DNA amplicon, the intensity of fluorescent emission in the plane parallel to the excitation plane increases. Typically, both parallel and perpendicular intensities are measured. The changes in total intensity are then compensated for by applying the formula:

$$P=(I_{PARA}-I_{PER})/(I_{PARA}+I_{PER}),$$

where:

$I_{PARA}$=Fluorescent intensity in the plane polarized in the plane polarized parallel to the plane of excitation polarication; and $I_{PFR}$=Fluorescent intensity in the plane polarized in the plane polarized perpendicular to the excitation polarization.

This formula yields the dimensionless quantity referred to as the polarization ratio (P).

Since it is the polarization intensity in the plane parallel to the excitation polarization which increases with increased hybridization, measuring the intensity of the polarization in the plane parallel to the excitation polarization over time will show the increase in hybridization over time. This is a kinetic or dynamic approach to the measurement of fluorescence polarization, which is also suitable for use with fluorescence energy transfer and light absorbance assays. By using such a kinetic or dynamic approach, compensation for absolute intensity becomes somewhat less important because each sample is measured against itself and is thus a relative measurement. In the case of a fluorescence polarization assay, therefore, it becomes necessary to measure fluorescence intensity only in the plane polarized parallel to the plane of the excitation polarization.

The kinetic or dynamic approach described above allows for the use of a confocal polarization method, where the polarizer for the excitation beam is also used as the polarizer for the fluorescence emitted by the sample, thereby reducing the number of required polarizing elements to one. This differs from the conventional approach, in which separate polarization elements are needed in the measuring instrument for both the excitation beam and the sensor used to detect the fluorescent emissions from the samples. With only a single polarizing element being required in the confocal method, this element can be provided in the DNA card 20 itself (i.e., in the form of a polarized sealing strip 32 or top layer 44) and need not be provided in the measuring instrument as in the prior art. Thus, standard microplate fluorometers containing no polarization elements can be used in the fluorescence polarization assay of the present invention. In the case of fluorescence energy transfer assays, standard microplate fluorometers can also be used, and in the case of light absorption assays, standard microplate readers can be used.

Figure 10:
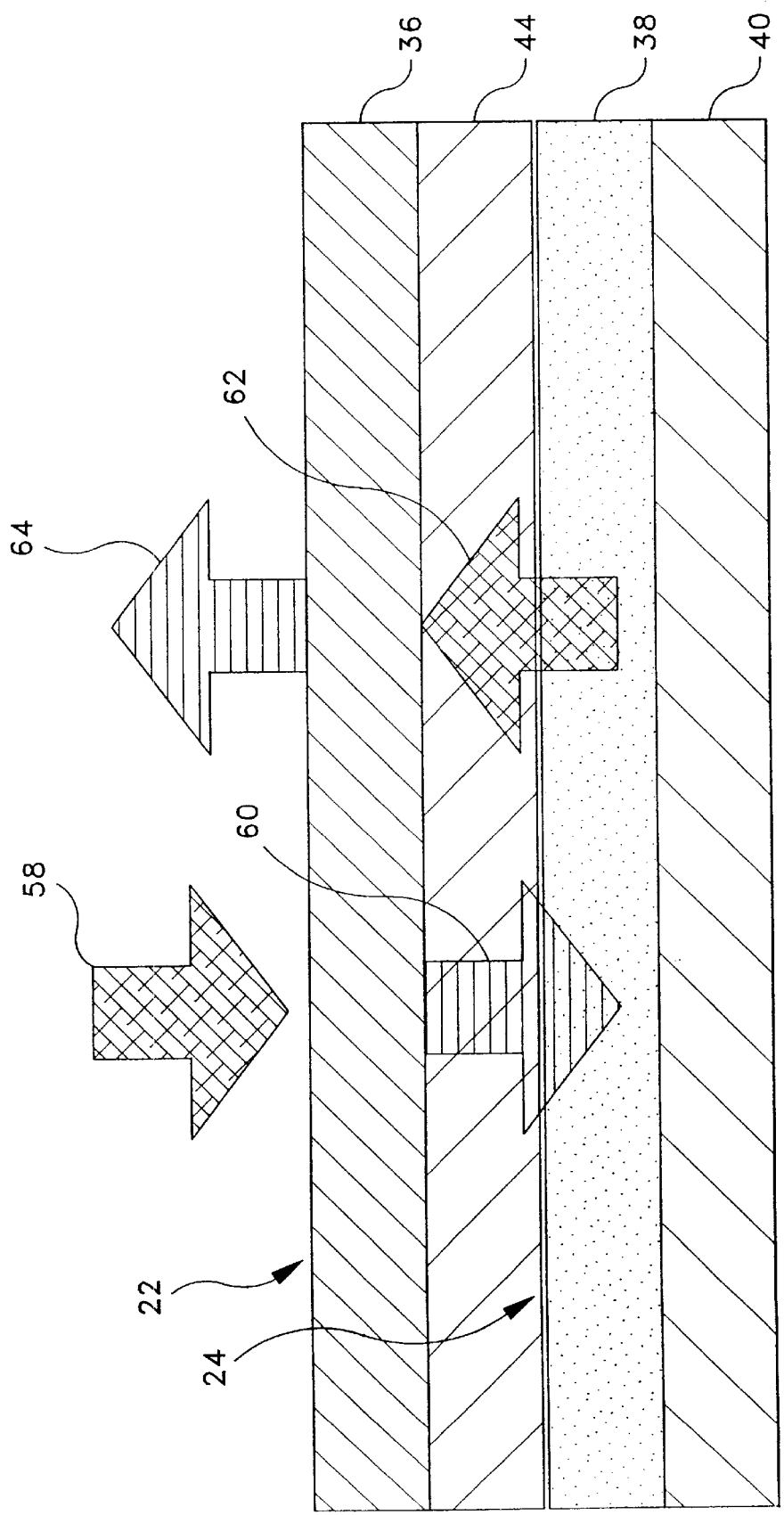
FIG. 10 is an enlarged sectional view through one of the discrete sample cells in the DNA amplification and DNA probe assay card of FIGS. 1–4, illustrating the manner in which the use of a light-polarizing, material for the sealing strips allows a confocal detection method to be used.

The enlarged cross-sectional view of FIG. 10 illustrates the sample chamber 24 of one sample cell 22 filled with a liquid biological sample 38 during a fluorescence polarization assay. In this example, the seal 36 is made of a plastic polarizing film, and serves as the confocal polarizer during the assay. The top layer 44 of the DNA card 20 is made of transparent, non-polarizing CAB. In operation, an unpolarized light beam 58 is directed toward the sample cell 22 containing the liquid biological sample 38. When the unpolarized light beam passes through the polarizing seal 36, the transmitted light beam 60 is of single polarization. The fluorescent DNA probes in the liquid biological sample 38 are excited by the polarized beam 60 and emit light (indicated by the arrow 62) of various polarizations. However, the same polarizing seal 36 polarizes these emissions in a plane parallel to that of the excitation beam 60, resulting in a polarized beam 64 being detected by the fluorometer. In this way, a confocal polarization method is implemented without requiring any polarization elements in the fluorometer itself.

Figure 11:
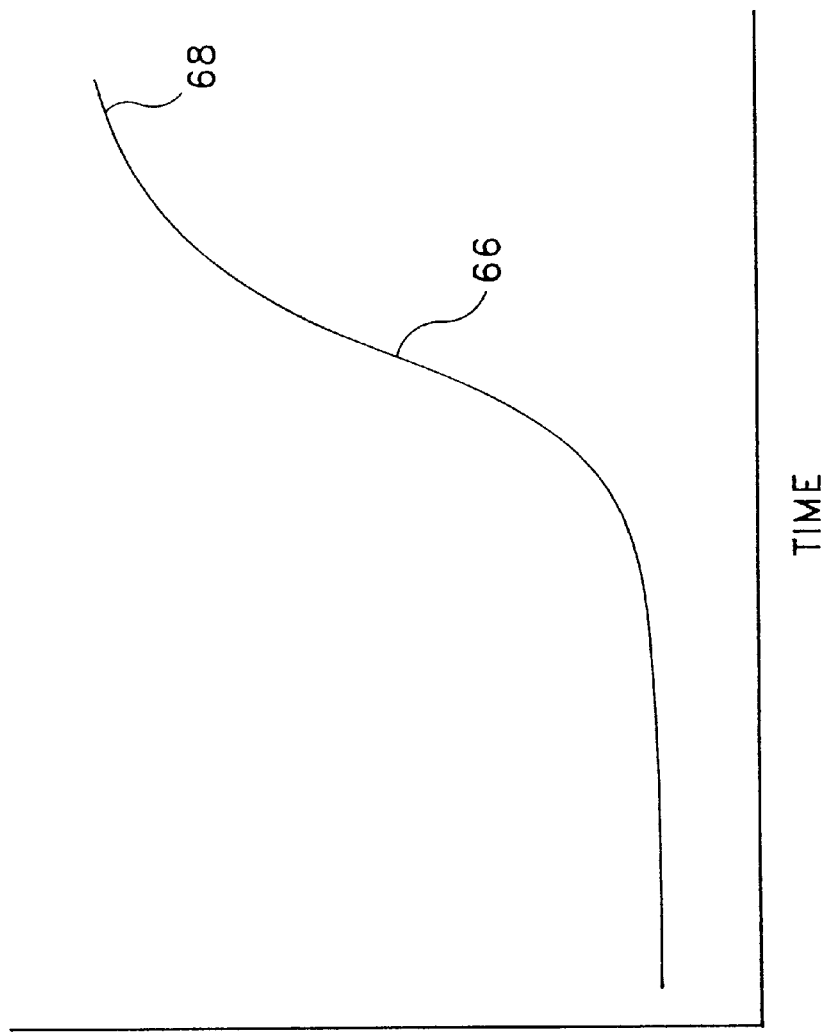
FIGS. 11 and 12 are graphs depicting the change in fluorescence intensity with time during a DNA amplification and homogeneous DNA fluorescence polarization assay.
Figure 12:
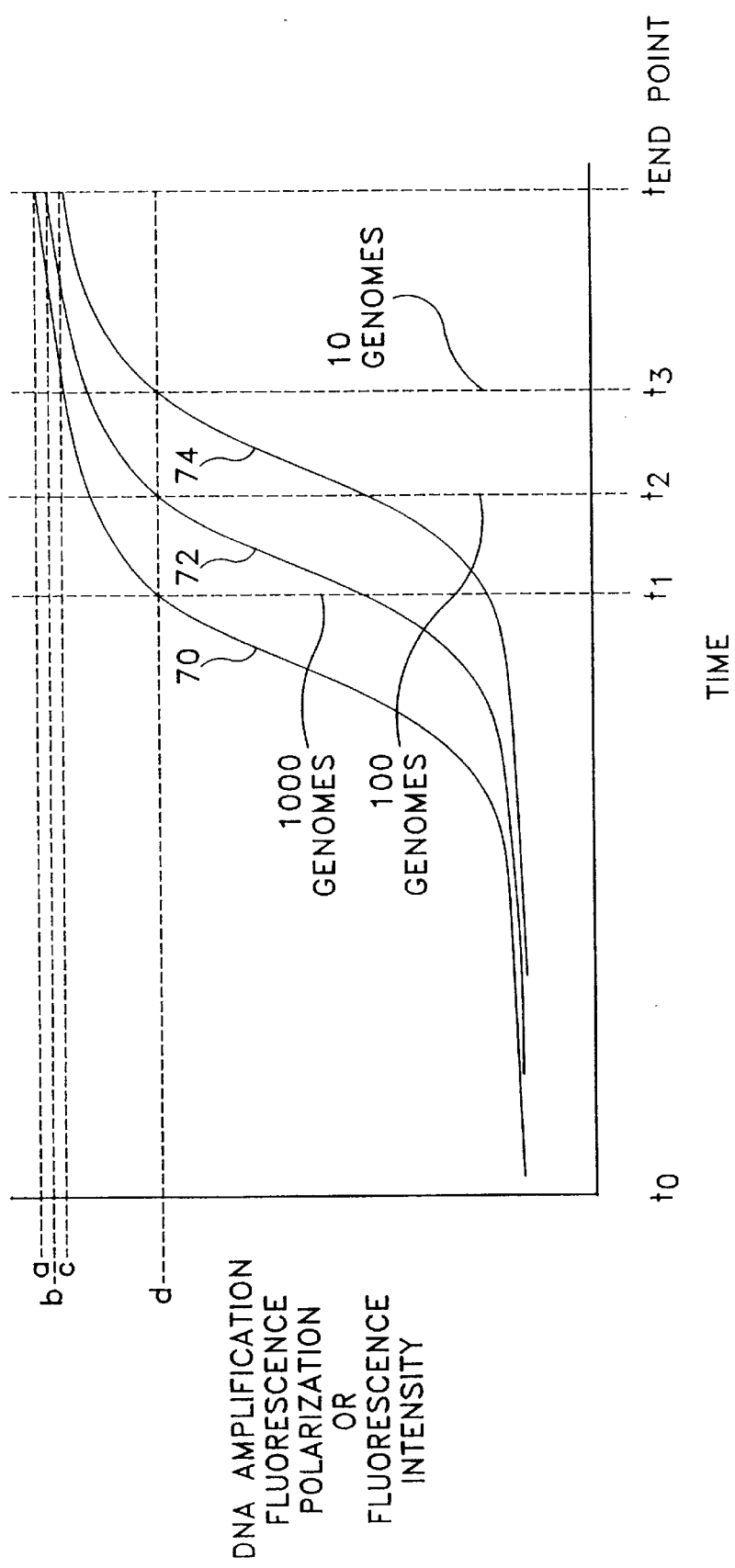

FIG. 11 is a graph of the typical relationship that homogeneous DNA amplification and assay reactions exhibit with respect to time. This relationship is similar whether assay reagents for fluorescence polarization, fluorescence energy transfer (fluorescence intensity) or light absorbance are used. The graph shows that the reactions exhibit an initial exponential portion 66, and a final linear portion 68. FIG. 12 depicts a graph similar to that of FIG. 11, but includes curves for three different concentrations of genomes. The concentrations used are 10 genomes, 100 genomes and 1000 genomes per unit volume. Typical DNA probe assays are performed on fully amplified samples, in which case they are end point reactions. DNA amplification reactions typically produce a maximum number of amplicons that is independent of the starting number of genomes. In FIG. 12, it can be seen that the 1000-genome curve exhibits its exponential phase 70 at a time before the 100-genome curve exhibits its exponential phase 72. Similarly, the 100-genome curve exhibits its exponential phase 72 at a time before the 10-genome curve exhibits its exponential phase 74.

However, by the time labelled $t_{end\,point}$, the magnitudes of all three curves are very similar and there is only a small difference between the 1000-genome, 100-genome and 10-genome curves, as shown by the points a, b and c on the vertical axis. By accumulating fluorescence intensity data during the entire time interval represented by any given one of the curves in FIG. 12 (i.e., between $t_0$ and $t_{end\,point}$), rather than simply taking the final reading at $t_{end\,point}$, information about the fluorescence polarization assay is available earlier and with better resolution. In addition, various different protocols may be used. For instance, by measuring the time to a given amplitude (point d in FIG. 12), it can be seen that the 1000-genome curve at time $t_1$ will be detected first and that its resolution from the 100-genome curve (at time $t_2$) is increased, as is the resolution of the 100-genome curve from that of the 10-genome curve at time $t_3$. Alternatively, examining the amplitudes of the three curves over time indicates that there are many places better than $t_{end\,point}$ to make measurements to resolve the differences in the three curves. If time $t_1$ is taken, for example, there is much better resolution between the 1000-genome curve and the 100-genome curve than at $t_{end\,point}$, and a similar increase in resolution exists between the 100-genome curve and the 10-genome curve at time $t_2$.

As noted previously, the nature of the measuring instrument with which the DNA card 20 is used will vary depending upon the construction of the DNA card 20 itself. For embodiments of the DNA card 20 containing polarizing elements, a typical microplate fluorometer with suitable thermal control can be used. For embodiments of the DNA card 20 that do not contain polarizing elements, a measuring instrument containing such elements in required. An example of such an instrument is shown in FIGS. 13–15.

Figure 13:
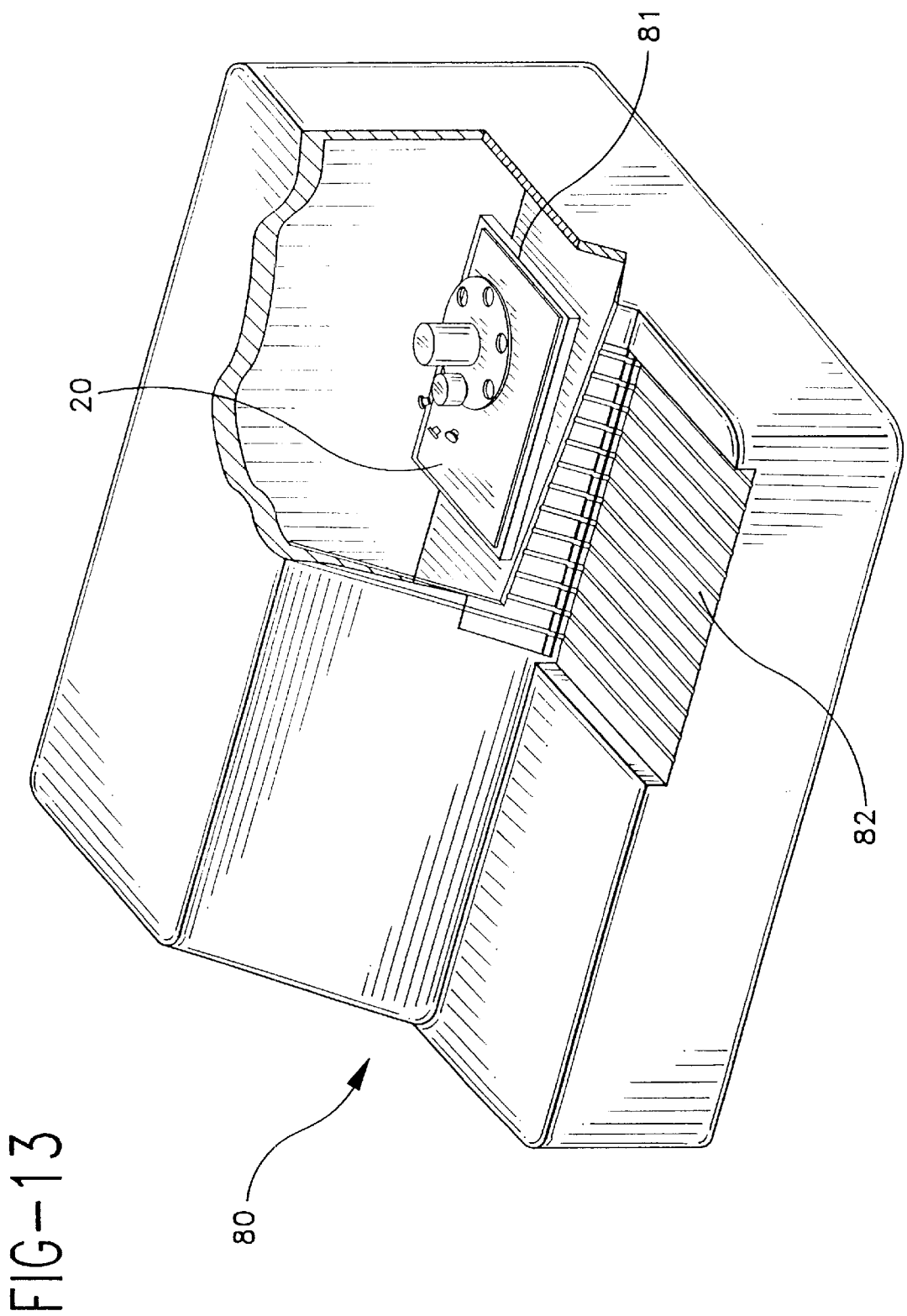

Referring first to FIG. 13, the measuring instrument 80 is shown in a perspective view with a portion cut away to illustrate the manner in which the DNA card 20 is received in the instrument. The DNA card 20 is initially placed on a heated carrier 81 which extends out over the front portion 82 of the instrument, and is then drawn automatically into the interior of the instrument at the position shown. In this position, shown in more detail in the enlarged view of FIG. 14, the DNA card 20 is located below three polarized laser diode sources 84 of different wavelengths such as 630 nm, 660 nm and 690 nm. A motor 86 selectively rotates a six-position polarized filter wheel 88 to position polarized wavelength filters 90, 92, 94 and 96 (and two additional filters which are not visible) above the sample cell 22 of interest. These filters match the emissions of the various fluorescent DNA probes and allow for the detection and measurement of these wavelengths by a photomultiplier tube (PMT) detector 98 in planes both parallel and perpendicular to the polarization plane of the input or source beam. The heated carrier 81 is indexed in the x and y directions (by means not shown) to address different ones of the sample cells 22.

Figure 14:
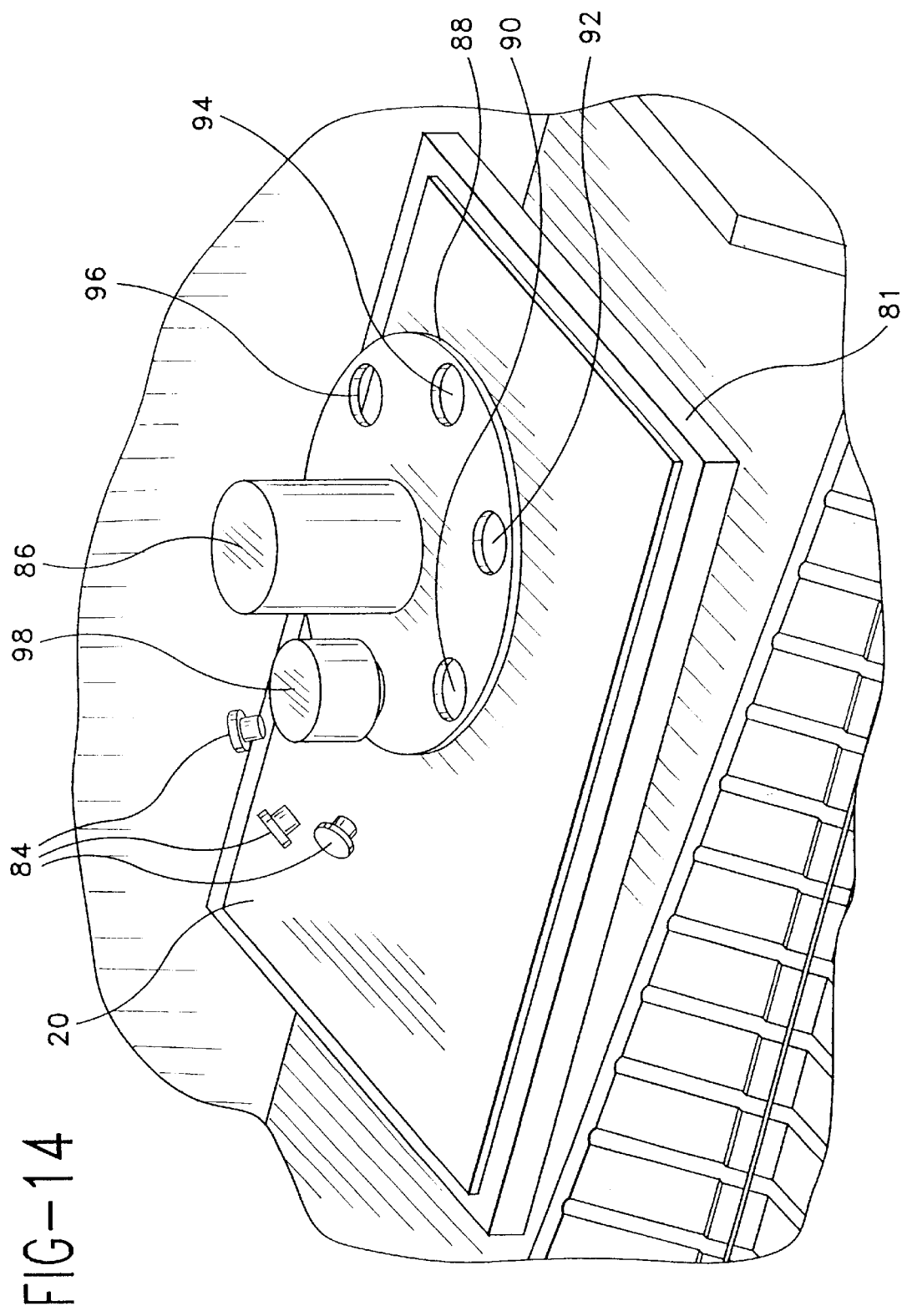

FIG. 15 is a front or edge-on view of the DNA card 20, of FIGS. 13 and 14, showing a single source 84 which provides a specular input beam 100 directed to a particular sample cell 22 of the DNA card 20. This beam is monochromatic and polarized as a consequence of having been generated by a laser diode source. If other types of sources are used, a polarizer and wavelength filter are required. When excited by the input beam 100, the fluorescent DNA probes in the sample cell 22 of the DNA card 20 emit light 102. The light 102 passes through the polarizer and wavelength filter of the filter wheel 88, to the PMT photodetector 98 for detection and measurement.

Examples of several different ways in which the DNA card 20 may be constructed are provided below. It should be understood that these examples are merely illustrative and are not intended to limit the scope of the present invention.

EXAMPLE 1

The DNA card 20 comprises a top layer 44 made of transparent, nonpolarizing CAB, a middle layer 42 made of black PVC, and a bottom layer 40 made of transparent, non-polarizing CAB. The sealing strips 32 have the configuration shown in FIG. 9A, and are made of a plastic polarizing film coated on one side with an optically clear pressure-sensitive adhesive. The resulting DNA card 20 can be used in a standard microplate fluorometer having no polarizing elements.

EXAMPLE 2

The DNA card 20 comprises a top layer 44 is made of a plastic polarizing film, a middle layer 42 made of black PVC, and a bottom layer 40 made of transparent, non-polarizing CAB. The sealing strips 32' are made of black PVC and have the configuration illustrated in FIG. 9B. The resulting DNA card 20 can be used in a standard microplate fluorometer having no polarizing elements.

EXAMPLE 3

The top layer 44, middle layer 42 and bottom layer 40 of the DNA card 20 are all made of transparent, non-polarizing CAB. The sealing strips 32 have the configuration shown in FIG. 9A, and are made of a transparent, non-polarizing CAB with an applied pressure-sensitive adhesive. When constructed with fluorescence polarization assay reagents, the resulting DNA card 20 is used in a measuring instrument containing polarizing elements as illustrated, for example, in FIGS. 13–15. Alternatively, this embodiment, when constructed with fluorescence energy transfer assay reagents, results in a DNA card 20 that is measured on a typical microplate fluorometer. This embodiment is also suitable for construction with light absorbance assay reagents, which am be measured on a typical microplate reader.

EXAMPLE 4

The DNA card 20 comprises a top layer 44 made of transparent, non-polarizing CAB, and a middle layer 42 and bottom layer 40 both made of black CAB. The sealing strips 32 have the configuration shown in FIG. 9A, and are made of a plastic polarizing film with an applied pressure-sensitive adhesive. The resulting DNA card 20 may be used with a conventional microplate fluorometer.

EXAMPLE 5

The top, middle and bottom layers 44, 42 and 40 of the DNA card 20 are as set forth in Example 4. However, the sealing strips 32' have the configuration shown in FIG. 9B, and are made of transparent, non-polarizing CAB with an applied pressure-sensitive adhesive. The resulting DNA card 20 is used in a measuring instrument of the type illustrated in FIGS. 13–15.

EXAMPLE 6

The top layer 44, middle layer 42 and bottom layer 40 of the DNA card 20 are as set forth in Example 3, and the sealing strips 32 have the configuration shown in FIG. 9a. However, the sealing strips 32 are made or a plastic polarizing film with an applied pressure-sensitive adhesive. The resulting DNA card 20 may be used with a conventional microplate fluorometer.

The foregoing is illustrative of the present invention, and is not to be construed as limiting thereof, as numerous alternatives to the devices and methods described which incorporate the present invention will be apparent to those skilled in the art. The invention is accordingly defined by the following claims with equivalence of the claims to be included therein.

That which is claimed is:

1. An apparatus for carrying out a homogeneous nucleic acid amplification and nucleic acid assay on a liquid biological sample, comprising:

a sample cell for receiving a liquid biological sample, said sample cell having a sample chamber in said sample cell;

a first opening which serves as a sample port for admitting said liquid biological sample into said sample chamber;

a second opening which serves as an air vent for allowing air to be displaced from said sample chamber during admission of said liquid biological sample into said sample cell; and a dried nucleic acid amplification reagent and a dried homogeneous nucleic acid assay reagent, said reagents being adhered to the interior of said sample chamber for reacting with said liquid biological sample.

2. An apparatus as claimed in claim 1, wherein said dried nucleic acid amplification reagent and said homogeneous nucleic acid assay reagent are provided in the form of a single spot adhered to an internal surface of said sample chamber.

3. An apparatus as claimed in claim 1, further comprising a sealing member attachable to said sample cell for sealing said sample port after said liquid biological sample has been admitted to said sample chamber.

4. An apparatus as claimed in claim 1, wherein said homogeneous nucleic acid assay reagent comprises a fluorescence polarization assay reagent, and wherein at least a portion of said sample cell is sufficiently light-transmissive to permit external detection of a fluorescence polarization reaction occurring in a liquid biological sample contained in said sample chamber.

5. An apparatus as claimed in claim 3, wherein:

said homogeneous nucleic acid assay reagent comprises a fluorescence polarization assay reagent;

at least a portion of said sample cell is sufficiently light-transmissive to permit external detection of a fluorescence polarization reaction occurring in a liquid biological sample contained in said sample chamber; and said sealing member is made of a light-transmissive material and is attachable over said light-transmissive portion of said sample chamber.

6. An apparatus as claimed in claim 5, wherein at least one of said sealing member and said light-transmissive portion of said sample chamber is made of a light-polarizing material.

7. An apparatus as claimed in 1, wherein:

said sample cell is formed in a laminated card-like member having a bottom layer forming a bottom wall of said sample chamber, an apertured middle layer forming side walls of said sample chamber, and a top layer forming an upper wall of said sample chamber, said sample port being formed in said top layer; and said sample cell is one of a plurality of sample cells disposed in a two-dimensional array across the length and width of said card-like member.

8. An apparatus as claimed in claim 7, further comprising a sealing member for sealing the sample ports of said sample cells after liquid biological samples have been admitted to said sample chamber, said sealing member comprising a layer of flexible material which is attachable to the top layer of said laminate by means of a pressure-sensitive adhesive carried on the underside of said layer of flexible material.

9. A method for carrying out an integrated nucleic acid amplification and homogeneous nucleic acid fluorescence detection reaction on a liquid biological sample comprising:

provic ing the apparatus of claim 1;

preheating the sample cell of said apparatus to a temperature suitable for nucleic acid amplification;

introducing a liquid biological sample into said preheated sample cell to bring said liquid biological sample into contact with said dried nucleic acid amplification reagent and said dried homogeneous nucleic acid fluorescence detection assay reagent;

equilibrating the temperature of said liquid biological sample to the temperature of said preheated sample cell; and after said temperature equilibration is complete, commencing said nucleic acid amplification reaction in said sample cell.

10. A method as claimed in claim 9, wherein the step of equilibrating the temperature of said liquid biological sample to the temperature of said preheated sample cell comprises forming a thin layer of said liquid biological sample in said sample cell to enhance heat transfer between said sample cell and said liquid biological sample.

11. A method as claimed in claim 9, wherein the time required for said temperature equilibration to occur is substantially the same as the time required for said liquid biological sample to dissolve said dried nucleic acid amplification reagent.

* * * * *